United States Patent [19]

Gillard et al.

[11] Patent Number: 5,308,850
[45] Date of Patent: May 3, 1994

[54] (BICYCLIC-HETERO-ARYLMETHOXY)INDOLES AS INHIBITORS OF LEUKOTRIENE BIOSYNTHESIS

[75] Inventors: John W. Gillard, Baie d'Urfe; John H. Hutchinson, Montreal; Richard Frenette; Michel Therien, both of Lavel, all of Canada

[73] Assignee: Merck Frosst Canada, Inc., Kirkland, Canada

[21] Appl. No.: 951,630

[22] Filed: Sep. 25, 1992

Related U.S. Application Data

[63] Continuation-in-part of Ser. No. 768,127, Sep. 30, 1991, abandoned.

[51] Int. Cl.$^5$ ............... A61K 31/435; A61K 31/425; C07D 495/04; C07D 275/04
[52] U.S. Cl. ..................... 514/301; 514/302; 514/367; 514/375; 514/382; 514/414; 546/114; 546/115; 548/159; 548/217; 548/221; 548/252; 548/253; 548/454
[58] Field of Search ............... 548/159, 217, 252, 221, 548/253, 454; 546/114, 115; 514/367, 375, 414, 301, 302, 382

[56] References Cited

U.S. PATENT DOCUMENTS

| 3,773,762 | 11/1973 | Nakao et al. | 548/500 |
| 4,629,733 | 12/1986 | Muiller et al. | 514/418 |
| 5,034,403 | 7/1991 | Effland et al. | 514/338 |
| 5,095,031 | 3/1992 | Brooks et al. | 514/419 |

FOREIGN PATENT DOCUMENTS

| 5639886 | 10/1986 | Australia . |
| 0166591 | 1/1986 | European Pat. Off. . |
| 0181568 | 5/1986 | European Pat. Off. . |
| 0275667 | 7/1988 | European Pat. Off. . |
| 0279263 | 8/1988 | European Pat. Off. . |
| 0419049 | 3/1991 | European Pat. Off. . |
| WO88/06886 | 3/1988 | PCT Int'l Appl. . |
| WO91/06537 | 5/1991 | PCT Int'l Appl. . |
| WO91/06538 | 5/1991 | PCT Int'l Appl. . |
| WO91/6539 | 5/1991 | PCT Int'l Appl. . |
| 92/03132 | 3/1992 | PCT Int'l Appl. . |
| 1228848 | 4/1971 | United Kingdom . |

OTHER PUBLICATIONS

Empey, Canadian J. Physiol. Pharmacology, 70, pp. 660–668 (1992).
Harper et al., J. Med. Chem., 35, pp. 1191–1200 (1992).
Shen et al., Advances in Drug Research, 12, pp. 89, 90, 143 & 144 (1977).
Sheinkman et al. Chem. Ab., vol. 67, 54017 (1967).
Biniecki et al. Chem. Ab., vol. 98, 197936 (1983).
Pakula et al., Chem. Ab., vol. 105, 190835 (1986).

*Primary Examiner*—Bernard Dentz
*Attorney, Agent, or Firm*—Sylvia A. Ayler; Mark R. Daniel; Joseph F. DiPrima

[57] ABSTRACT

Compounds having the formula I:

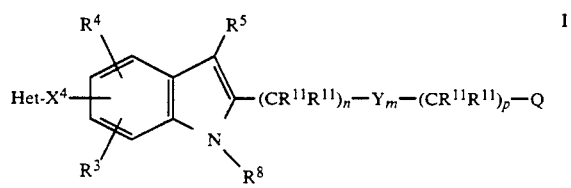

are inhibitors of leukotriene biosynthesis. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

7 Claims, No Drawings

(BICYCLIC-HETERO-ARYLMETHOXY)INDOLES AS INHIBITORS OF LEUKOTRIENE BIOSYNTHESIS

CROSS-REFERENCE

This is a continuation-in-part of Ser. No. 768,127, filed Sep. 30, 1991, now abandoned.

BACKGROUND OF THE INVENTION

European Patent Applications 166,591 and 275,667 disclose a series of indole-based compounds with activity as prostaglandin antagonists and inhibitors of leukotriene biosynthesis respectively. In EP 181,568 and EP 200,101 are disclosed a series of compounds, containing two aromatic nuclei, which are described as possessing activity as lipoxygenase inhibitors. In EP 279,263 is disclosed a series of indoles, benzofurans and benzothiophenes which are described as possessing activity as lipoxygenase inhibitors. U.S. Pat. No. 4,629,733 describes novel indolinones which are antithrombotic and inhibit both phosphodiesterase and tumor metastasis. The chemical preparation of quinolylindoles is referred to by Sheinkman, et al., Chem. Ab., Vol. 67, 54017 (1967), without mentioning any utility for such compounds. A number of N-acyl derivatives of indole-3-acetic acid are described as potential anti-inflammatory agents by Biniecki, et al., Chem. Ab., Vol. 98, 197936 (1983), by Pakula, et al., Chem. Ab., Vol. 105, 190835 (1986), and in British Pat. Spec. 1,228,848.

EP 419,049 (Mar. 27, 1991) teaches (quinolin-2-ylmethoxy)indoles as inhibitors of leukotriene biosynthesis.

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

DETAILED DESCRIPTION OF THE INVENTION

The present invention provides novel compounds of the formula I:

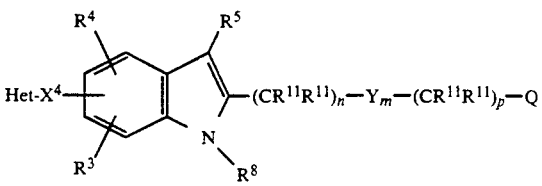

wherein:

Het is $ArR^1R^2$;

Ar is a bicyclic aromatic ring containing 8 or 9 members, one of which is O or S, and 0–2 of which is N, and the N-oxides thereof;

$R^1$, $R^2$, $R_3$, $R^4$ and $R^{10}$ are independently hydrogen, halogen, perhalo lower alkenyl, lower alkyl, lower alkenyl, lower alkynyl, $-CF_3$, $-CN$, $-NO_2$, $-N_3$, $-C(OH)R^{11}R^{11}$, $-CO_2R^{12}$, $-SR^{14}$, $-S(O)R^{14}$, $-S(O)_2R^{14}$, $-S(O)_2NR^{15}R^{15}$, $-OR^{15}$, $-NR^{15}R^{15}$, $-C(O)R^{16}$ or $-(CH_2)_rR^{21}$;

$R^5$ is hydrogen, $-CH_3$, $CF_3$, $-C(O)H$, $X^1-R^6$ or $X^2-R^7$;

$R^6$ and $R^9$ are independently alkyl, alkenyl, $-(CH_2)_uPh(R^{10})_2$ or $-(CH_2)_uTh(R^{10})_2$;

$R^7$ is $-CF_3$ or $R^6$;

$R^8$ is hydrogen or $X^3-R^9$;

each $R^{11}$ is independently hydrogen or lower alkyl, or two $R^{11}$'s on same carbon atom are joined to form a cycloalkyl ring of 3 to 6 carbon atoms;

$R^{12}$ is hydrogen, lower alkyl or $-CH_2R^{21}$;

$R^{13}$ is lower alkyl or $-(CH_2)_rR^{21}$;

$R^{14}$ is $-CF_3$ or R13;

$R^{15}$ is hydrogen, $-COR^{16}$, $R^{13}$, or two $R^{15}$'s on the same nitrogen may be joined to form a monocyclic heterocyclic ring of 4 to 6 atoms containing up to 2 heteroatoms chosen from O, S, or N;

$R^{16}$ is hydrogen, $-CF_3$, lower alkyl, lower alkenyl, lower alkynyl or $-(CH_2)_rR^{21}$;

$R^{17}$ is $-(CH_2)_s-C(R^{18}R^{18})-(CH_2)_s-R^{19}$ or $-CH_2CONR^{15}R^{15}$;

$R^{18}$ is hydrogen or lower alkyl;

$R^{19}$ is
  a) a monocyclic or bicyclic heterocyclic ring containing from 3 to 9 nuclear carbon atoms and 1 or 2 nuclear heteroatoms selected from N, S or O and with each ring in the heterocyclic radical being formed of 5 or 6 atoms, or
  b) the radical $W-R^{20}$;

$R^{20}$ is alkyl or $-COR^{23}$;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;

$R^{23}$ is alkyl, cycloalkyl, or monocyclic monoheterocyclic ring;

$R^{24}$ is the residual structure of a standard amino acid, or $R^{18}$ and $R^{24}$ attached to the same N can cyclize to form a proline residue;

m is 0 or 1;
n is 0 to 3;
p is 1 to 3 when m is 1;
p is 0 to 3 when m is 0;
r is 0 to 2;
s is 0 to 3;
t is 0 to 2;
u is 0 to 3;
w is O, S or $NR^{15}$;
$X^1$ is O or $NR^{15}$;
$X^2$ is CO, $CR^{11}R^{11}$, S, S(O), or $S(O)_2$;
$X^3$ is CO, $CR^{11}R^{11}$, $S(O)_2$, or a bond;
$X^4$ is CH=CH, $CH_2-Y^1$, or $Y^1-CH_2$;
Y is $X^1$ or $X^2$;
$Y^1$ is O, S, $S(O)_2$, or $CH_2$;
Q is $-CO_2R^{12}$, $-CONHS(O)_2R^{14}$, $-S(O)_2NHR^{15}$, $-CONR^{15}R^{15}$, $-CO_2R^{17}$, $-CONR^{18}R^{24}$, $-CR^{11}R^{11}OH$, or 1H— or 2H-tetrazol-5-yl;
or a pharmaceutically acceptable salt thereof.

A preferred embodiment of Formula I is that in which $X^4$ is $CH_2-Y^1$, $Y^1$ is O, and the remaining sustituents are as defined for Formula I.

Another preferred embodiment of Formula I is that in which
$R^1$, $R^2$, $R^3$, and $R^4$ are hydrogen;
$R^5$ is $X^2-R^7$;
$R^7$ is $R^6$;
$R^8$ is $R^9$;
$R^{10}$ is hydrogen or halogen;
m is 0;
n is 1 to 3;
u is 0 in $R^6$ and 1 in $R^9$;
$X^2$ is $CR^{11}R^{11}$ or S;
$X^4$ is $CH_2-Y^1$;
$Y^1$ is O;
Q s $-CO_2R^{12}$ or 1-H or 2H-tetrazol-5-yl; and the remaining substituents are as defined for Formula I;
or a pharmaceutically acceptable salt thereof.

Definitions

The following abbreviations have the indicated meanings:
Me=methyl
Bn=benzyl
Ph=phenyl
DIBAL-N=diisobutyl alumnium hydride
HMPA=hexamethylphosphorictriamide
KHMDS=potassium hexamethyldisilazide
t-Bu=tert-butyl
i-Pr=isopropyl
c-$C_6H_{11}$=cyclohexyl
c-Pr=cyclopropyl
c-=cyclo
Ac=acetyl
Tz=1H- or 2H- tetrazol-5-yl
Th=2- or 3- thienyl
c-$C_5H_9$=cyclopentyl
1-Ad=1-adamantyl
NBS=N-bromosuccinimide
NCS=N-chlorosuccinimide Alkyl, alkenyl, and alkynyl are intended to include linear, branched, and cyclic structures and combinations thereof.

"Alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, cyclododecyl, adamantyl, and the like.

"Lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

"Cycloalkyl" refers to a hydrocarbon ring having from 3 to 7 carbon atoms. Examples of cycloalkyl groups are cyclopropyl, cyclopentyl, cycloheptyl, and the like.

"Lower alkenyl" means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

"Lower alkynyl" means alkynyl groups of 2 to 7 carbon atoms. Examples of lower alkynyl groups include ethynyl, propargyl, 3-methyl-1-pentynyl, 2-heptynyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

The term "monocyclic monoheterocyclic ring" which defines $R^{23}$ means monocyclic groups of 5 to 7 members containing only 1 heteroatom selected from N, S or O in the ring. Examples include tetrahydrofuran, tetrahydrothiophene, pyrrolidine, piperidine, tetrahydropyran, and the like.

The term "monocyclic or bicyclic heterocyclic ring" which defines $R^{19}$ may be 2,5-dioxo-1-pyrrolidinyl, (3-pyridinylcarbonyl) amino, 1,3-dihydro-1,3-dioxo-2H-isoindol-2-yl, 1,3-dihydro-2H-isoindol-2-yl, 2,4-imidazolinedion-1-yl, 2,6-piperidinedion-l-yl, 2-imidazolyl, 2-oxo-1,3-dioxolen-4-yl, piperidin-1-yl, morpholin-1-yl, piperazin-1-yl, and the like.

"Bicyclic aromatic ring containing 8 or 9 members, one of which is O or S, and 0–2 of which is N, and the N-oxides thereof" which defines "Ar" may include benzofuran, benzoxazole, benzo-2,1,3-oxadiazole, furo[2,3-b]pyridine, furo[3,2-b]pyridine, furo[2,3-b]pyrazine, benzothiophene, benzisothiazole, benzothiazole, benzo-2,1,3-thiadiazole, thieno[2,3-b]-pyridine, thieno[3,2-b]pyridine, thieno[2,3-b]pyrazine, and the like.

The point of attachment of any heterocyclic ring may be at any free valence of the ring.

The term standard amino acid is employed to include the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F.H.C. Crick, Symposium of the Society for Experimental Biology, 1958 (12) p. 140.)

It is understood that $R^1$ and $R^2$ may be located at any free positions of Ar.

The terms $Ph(R^{10})_2$ and $Th(R^{10})_2$ indicate a phenyl or thienyl group substituted with two $R^{10}$ substituents.

Halogen includes F, Cl, Br, and I.

It is intended that the definitions of any substituent (e.g., $R^1$, $R^2$, $R^{15}$, $Ph(R^{10})_2$, etc.) in a particular molecule be independent of its definitions elsewhere in the molecule. Thus, $-NR^{15}R^{15}$ represents $-NHH$, $-NHCH_3$, $-NHC_6H_5$, etc.

The monocyclic heterocyclic rings formed when two $R^{15}$ groups join through N include pyrrolidine, piperidine, morpholine, thiamorpholine, piperazine, and N-methylpiperazine.

The prodrug esters of Q (i.e., when $Q=CO_2R^{17}$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987).

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzene-sulfonic, benzoic, camphorsulfonic, citric, ethane-sulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology, and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug (NSAID) that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |

| -continued | |
|---|---|
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

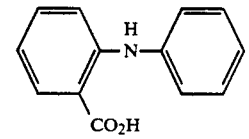

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

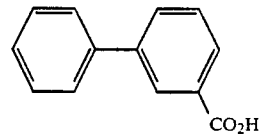

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

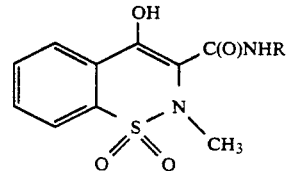

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDS, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones; and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethyl-histidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxy-chromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Compounds of the present invention can be prepared according to the following methods. Temperatures are in degrees Celsius.

The starting methoxy phenylhydrazines II are either commercially available or are described in the chemical literature as are the acetamidophenols XXVI. The benzyl phenylhydrazine starting materials III are prepared as described in EP 166,591 (17102 IA) and the ketones IV and XXXI are prepared as described in EP 166,591 and EP 275,667 (17496 IA). The 2-(halomethyl)quinolines VII are available from literature methods described in "Quinolines" Parts I and II, G. Jones (ED.), John Wiley & Sons, Toronto, 1977 and 1982. The preparation of VII by halogenation of the corresponding 2-methylquinolines is also described in the Jones'-volumes. The benzyl halides, $(R^{10})_2$ $PhCH_2$-Hal, are readily prepared and many such compounds are described in the prior art, such as U.S. Pat. No. 4,808,608 (17323 IB). Hal in VII and $(R^{10})_2$ $PhCH_2$-Hal represents Cl, Br or I.

Many syntheses of indoles are well-known in the chemical literature: see for example, "Heterocyclic compounds" Volume 25, Parts I, II, III, W.J. Houlihan (Ed.), Interscience, J. Wiley & Sons, N.Y., 1979, and "The Chemistry of Indoles" by R.J. Sundberg, Academic Press, N.Y., 1970. One of the most common syntheses is known as the Fischer Indole Synthesis, and is abbreviated in the following methods as "Fischer".

The $-CO_2H$ and $-CO_2R^{12}$ groups in the intermediates and final products in the various methods can be transformed to other representatives of Q such as $-CONHS(O)_2R^{14}$, $-NHS(O)_2R^{14}$, $-CONR^{15}R^{15}$, $-CH_2OH$ or tetrazol-5-yl by the methodology described in U.S. Pat. No. 4,808,608 (17323IB). The preparation of the pro-drug forms (Q is $-CO_2R^{17}$) from the acids may be effected by the methodology of EP 104,885 (16830 IA).

It will be apparent to one skilled in the art that the various functional groups ($R^1$, $R^2$, Y, Q, etc.) must be chosen so as to be compatible with the chemistry being carried out. Such compatibility can often be achieved by protecting groups, or by specific variations in the sequence of the reactions.

When $R^5$ is $S-R^7$, the corresponding sulfoxides and sulfones can be prepared by oxidation of the sulfides with one or two equivalents of an oxidizing agent such as m-chloroperbenzoic acid or monoperoxyphthalic acid or oxone (Trost, J. Org. Chem., 1988, pg.532).

Many of the following methods involve a basic hydrolysis of an ester function to obtain the corresponding carboxylic acid. In all cases, the free acid is obtained by acidification of the reaction mixture with a suitable acid such as hydrochloric, sulfuric, acetic, trifluoroacetic acid, etc.

Compounds 6, 10, 11, 16, 17, 19, 23, 24, 27, 28, and their precursor esters are all examples of the Formula I compounds of the present invention.

Compounds identified by Roman numerals (IV, V, XIV, XXVI, XXXI, and XXXV) are known and correspond to those compounds in EP 419,049, which is incorporated herein by reference.

METHOD 1

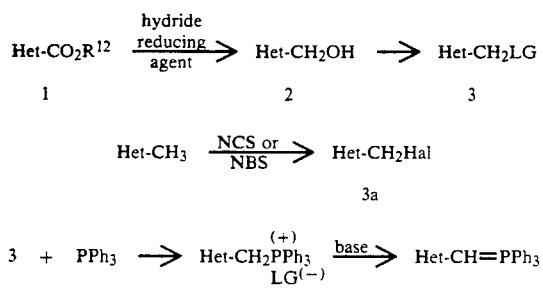

METHOD 2

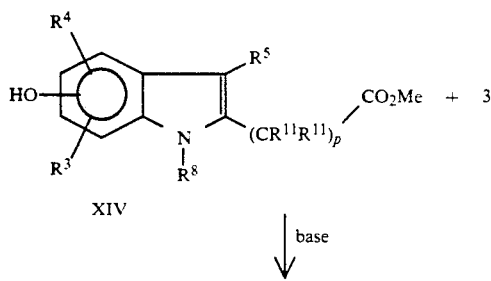

-continued

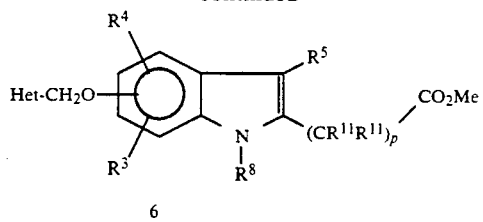

Method 1

The carboxy derivative 1- may be reduced by a suitable hydride reducing agent such as lithium aluminum hydride, sodium borohydride, DIBAL-H, or the like in appropriate solvents such as ether, THF, hexane, toluene, or mixtures thereof, to obtain alcohol 2. The alcohol function of 2 can be converted to a suitable leaving group (LG) such as a halide, or a sulfonate ester (mesylate, tosylate, triflate, etc.) by methods well known in the art to produce intermediate 3. A useful subgroup of 3 can be prepared by halogenation of the methyl compound Het-CH$_3$ by heating with halogenating agents such as NCS or NBS in appropriate solvents such as carbon tetrachloride, benzene, and the like.

Reaction of 3 with triphenylphosphine in ether, acetonitrile, THF, or similar solvents produces the phosphonium salt 4. Compound 4 is converted into the ylid 5 by treating with a base such as Et$_3$N, sodium hydride, butyl lithium, or an alkoxide, depending upon the reactivity of the phosphonium salt 4.

Method 2

Compound 3 is reacted with phenol XIV, in the presence of a suitable base such as potassium or cesium carbonate in a suitable solvent such as acetone, acetonitrile, or DMF to yield compound 6 which can be converted to its corresponding carboxylic acid by standard procedures.

METHOD 3

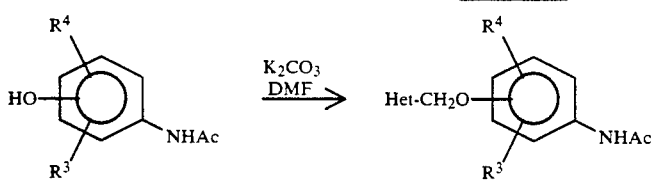

-continued
METHOD 3

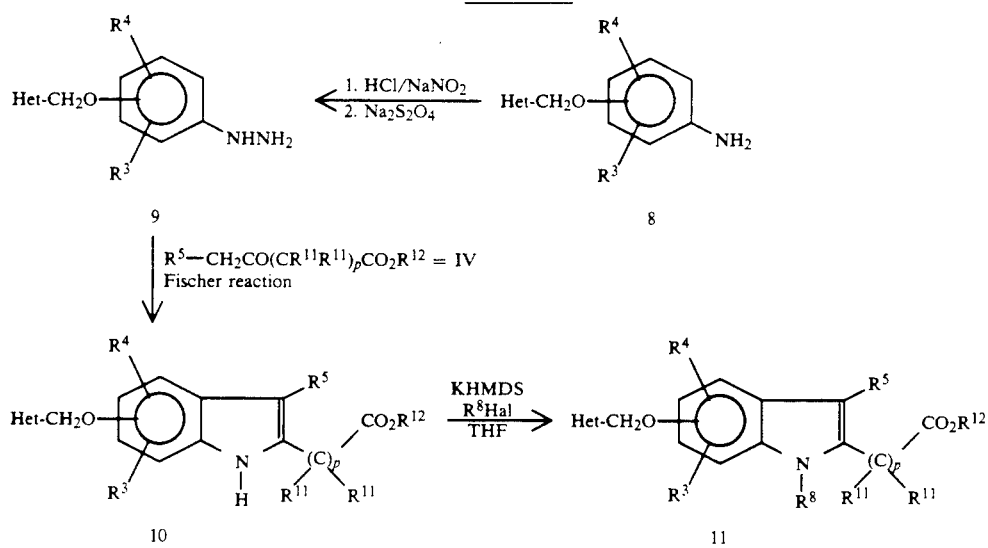

Method 3

A suitable N-acetylated aminophenol XXVI is reacted with 3 using an alkali hydride or carbonate, such as potassium carbonate as a base in a polar solvent like DMF or NMP. The resulting acetanilide 7 is then deacetylated using standard basic conditions, preferably using alcoholic potassium hydroxide under reflux to produce the aniline derivative 8. Conversion of the aniline derivative to the hydrazine analogue 9 is effected through reduction of the intermediate diazonium salt using sodium hydrosulfite in an aqueous medium.

The hydrazine 9 is then processed using a Fischer indolization with ketone IV to produce compound 10, which is then alkylated on the indole nitrogen using $R^8$-Hal and a suitable base such as KHMDS in THF or NaH in DMF to give compound 11.

METHOD 4

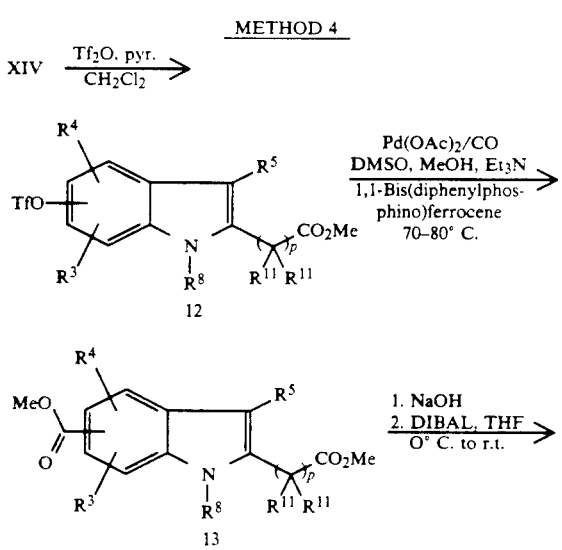

-continued
METHOD 4

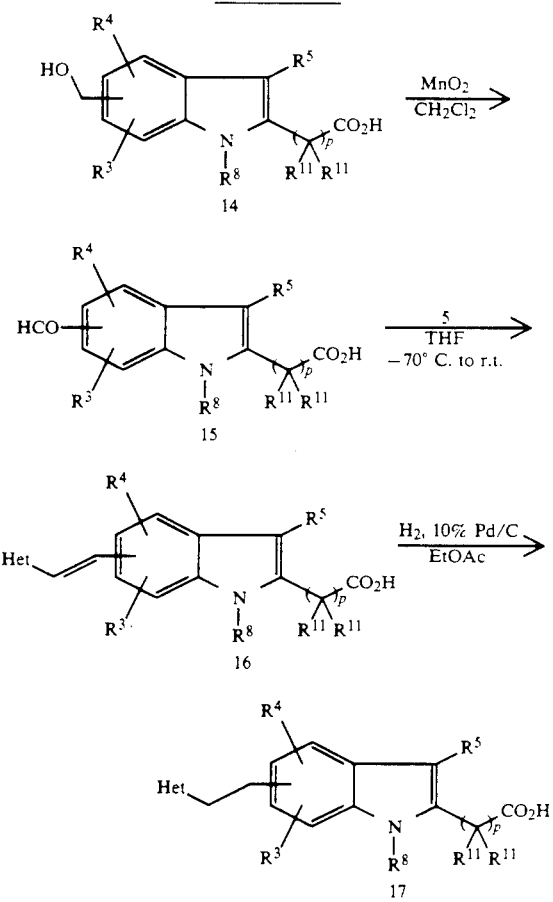

Method 4

Indole phenol XIV is transformed to a phenol triflate 12 by treatment with trifluoromethyl sulfonic anhydride ($Tf_2O$) in a solvent like pyridine in dichloromethane. The phenol triflate may be carboxymethylated to a compound like 13 under palladium acetate catalysis in an atmosphere of carbon monoxide, a phosphine ligand like 1,1-bis(diphenylphosphinoferrocene) enhances this reaction. Reduction of the carboxymethylated indole may be effected with a variety of hydride reducing agents. Conveniently, DIBAL-H is used in THF on the hydrolysed ester. The reduced carbinol product 14 is conveniently oxidized to a formylated derivative 15 with manganese dioxide in methylene chloride as a typical solvent. Aldehyde 15 can then be homologated under carbanion conditions, typically using Wittig reagent 5 as shown in the method, under anydrous conditions in an etherial solvent like THF. The temperature of this reaction is typically from −70° C. to room temperature. Indole styryl analogues (trans) 16 are thus formed. Further transformation of the styryl system may be effected by catalytic reduction using $H_2$ and Pd/C in an organic solvent like ethyl acetate to yield the saturated compound 17.

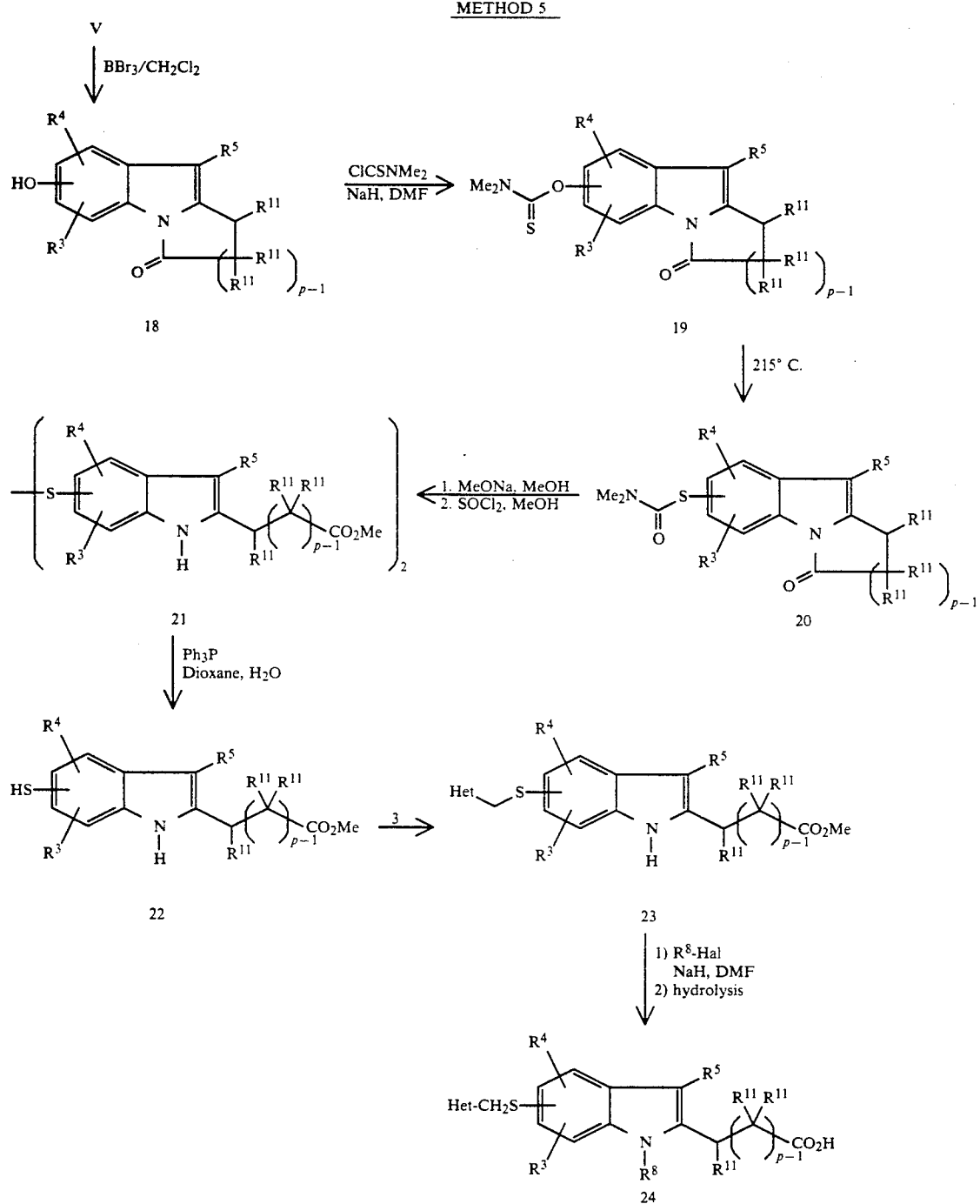

Method 5

Indole thio analogues of I such as 23 and 24 are conveniently prepared by the sequence shown in Method 5. The treatment of compound V with $BBr_3$ in a chlorinated solvent such as $CH_2C_2$ cleaves both the methyl ether and the indole N-benzyl group and cyclizes the product to an indole lactam 18. Derivatization of this compound as an N,N-dimethylthiocarbamoyl indole 19 followed by thermal rearrangement at >200° C. gives rise to an N,N-dimethylcarbamoylthioindole derivative 20. Depending on the duration of heating, dethiolation ($R^5 = -S-t-Bu \rightarrow R^5 = H$) may also take place. The hydrolysis of 20 may be effected using strong base, typically sodium methoxide in methanol is used. Spontaneous formation of disulfide 21 may occur in this reaction. The reduction of 21 can be achieved using triphenylphosphine in aqeuous dioxane to produce 22. Coupling of 22 to an appropriately substituted derivative 3 takes place under organic base catalysis. Typically triethylamine, in an organic solvent such as methylene chloride, is used. Transformation of indole 23 to an N-substituted derivative 24 is achieved under standard conditions described in Method 3.

METHOD 6

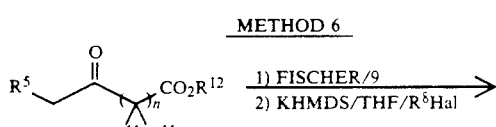

XXXI

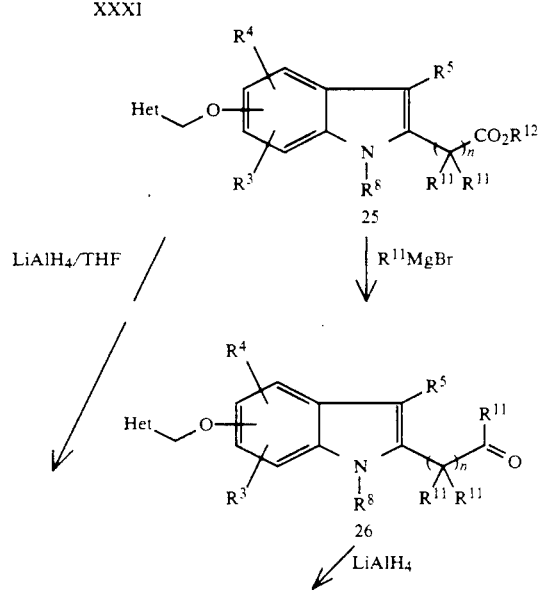

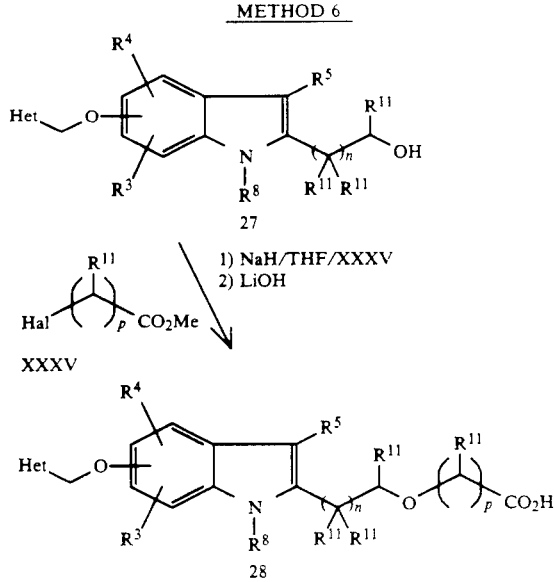

Method 6

Hydrazine 9 may also be transformed directly to unsubstituted indoles by a Fischer reaction with various ketones like XXXI. N-Alkylation of the indoles is effected using the conditions described in Method 3 to produce hetmethoxyindole alkanoate esters 25. Such esters are transformed to ketones or carbinols via Grignard conditions using alkyl magnesium halides in ether solvents like diethyl ether or through the use of lithium aluminum hydride in ether solvents like THF. The carbinols 27 so produced may be further transformed into ester compounds of the present invention by reacting with halo esters XXXV using sodium hydride as base in a suitable solvent like THF. Subsequent hydrolysis of the esters leads to acid compounds 28 of the present invention.

METHOD 7

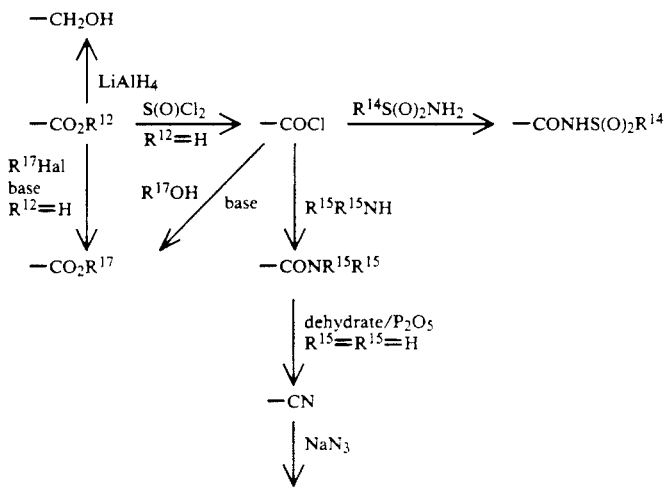

METHOD 7

1H- or 2H-tetrazol-5-yl

Method 7

The preparation of the various definitions of Q is outlined in Method 7, starting from the readily available carboxylic acid derivative —$CO_2R^{12}$. It will be obvious to one skilled in the art that many of the reactions indicated are reversible. Thus, by way of illustration, the —CN group can serve as the starting material to prepare the amide and carboxylic acid functional groups. The reactions depicted in Method 7, as well as methods for synthesis of the sulfonamide group (—$S(O)_2NHR^{15}$), are well-known in the art. See, for instance, the following textbooks:

1. J. March, *Advanced Organic Chemistry*, 3rd ed., J. Wiley and Sons, Toronto, 1985;
2. S. R. Sandler and W. Karo, *Organic Functional Group Preparations, I & II*, Academic Press, Toronto, 1983 and 1986.

Representative Compounds

Table I illustrates compounds representative of the present invention.

Assays for Determining Biological Activity

Compounds of Formula I can be tested using the following assays to determine their mammalian leukotriene biosynthesis inhibiting activity.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mm HEPES adjusted to pH 7.4 with NAOH). The cells are pelleted (350×g, 5 min.), resuspended in buffer with vigorous shaking, filtered through lens paper, recentrifuged and finally suspended in buffer at a concentration of 10 cells/ml. A 500 mL aliquot of PMN suspension and test compound are preincubated for 2 minutes at 37° C., followed by the addition of 10 MM A-23187. The suspension is stirred for an additional 4 minutes then bioassayed for $LTB_4$ content by adding an aliquot to a second 500 mL portion of the PMN at 37° C. The $LTB_4$ produced in the first incubation causes aggregation of the second PMN,

TABLE I

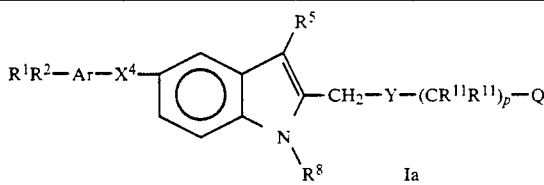

| Ex No. | $R^1/R^2$ | Ar | $X^4$ | $R^5$ | $R^8$ | $Y-(CR^{11}R^{11})_p-Q$ |
|---|---|---|---|---|---|---|
| 1 | H/H | benzo[b]furan-2-yl | $CH_2O$ | Me | $CH_2Ph-4-Cl$ | $C(Me)_2CO_2H$ |
| 2 | 5-Cl/H | benzothiazol-2-yl | $CH_2O$ | S-t-Bu | $CH_2Ph-4-Cl$ | $C(Me)_2CO_2H$ |
| 3 | H/H | thieno[2,3-b]pyridin-6-yl | $CH_2S$ | $COCH_2$-t-Bu | $CH_2Ph-3-CN$ | $C(Me)_2CONHS(O)_2Me$ |
| 4 | H/H | furo[3,2-b]pyridin-5-yl | $CH_2CH_2$ | S—Ph | $CH_2PhS(O)_2Me$ | $C(Me)_2CHOHMe$ |
| 5 | H/H | benzothiazol-2-yl | $CH_2O$ | S-t-Bu | $CH_2Ph-4-Cl$ | $C(Me)_2CO_2H$ |
| 6 | 5-F/H | benzothiazol-2-yl | $CH_2O$ | S-t-Bu | $CH_2Ph-4-Cl$ | $C(Me)_2CO_2H$ |
| 7 | 5-$CF_3$/H | benzothiazol-2-yl | $CH_2O$ | S-t-Bu | $CH_2Ph-4-Cl$ | $C(Me)_2CO_2H$ |
| 8 | 6-OMe/H | benzothiazol-2-yl | $CH_2O$ | S-t-Bu | $CH_2Ph-4-Cl$ | $C(Me)_2CO_2H$ |
| 9 | 2-Me/H | benzothiazol-5-yl | $CH_2O$ | S-t-Bu | $CH_2Ph-4-Cl$ | $C(Me)_2CO_2H$ |
| 10 | 5,6-$F_2$ | benzothiazol-2-yl | $CH_2O$ | S-t-Bu | $CH_2Ph-4-Cl$ | $C(Me)_2CO_2H$ |
| 11 | H/H | benzothiazol-2-yl | $CH_2O$ | $COCH_2$-t-Bu | $CH_2Ph-4-Cl$ | $C(Me)_2CO_2H$ |
| 12 | H/H | benzoxazol-2-yl | $CH_2O$ | S-t-Bu | $CH_2Ph-4-Cl$ | $C(Me)_2CO_2H$ |
| 13 | H/H | benzothiazol-2-yl | $CH_2O$ | Me | $CH_2Ph-4-Cl$ | $C(Me)_2CO_2H$ |
| 14 | H/H | benzothiazol-2-yl | $CH_2O$ | t-Bu | $CH_2Ph-4-Cl$ | $C(Me)_2CO_2H$ |
| 15 | H/H | benzothiazol-2-yl | $CH_2O$ | H | $CH_2Ph-4-Cl$ | $C(Me)_2CO_2H$ |
| 16 | H/H | benzothiazol-2-yl | $CH_2O$ | CO-c-Bu | $CH_2Ph-4-Cl$ | $C(Me)_2CO_2H$ |
| 17 | H/H | benzothiazol-2-yl | $CH_2O$ | $CH_2$-c-Bu | $CH_2Ph-4-Cl$ | $C(Me)_2CO_2H$ |
| 18 | 5-F/H | benzothiazol-2-yl | $CH_2O$ | $COCH_2$-t-Bu | $CH_2Ph-4-Cl$ | $C(Me)_2CO_2H$ |
| 19 | H/H | benzothiazol-2-yl | $CH_2O$ | CO-t-Bu | $CH_2Ph-4-Cl$ | $C(Me)_2CO_2H$ |
| 20 | H/H | benzothiazol-2-yl | $CH_2O$ | $CH_2$-t-Bu | $CH_2Ph-4-Cl$ | $C(Me)_2CO_2H$ |
| 21 | 5-F/H | benzothiazol-2-yl | $CH_2O$ | CO-t-Bu | $CH_2Ph-4-Cl$ | $C(Me)_2CO_2H$ |
| 22 | 5-F/H | benzothiazol-2-yl | $CH_2O$ | $CH_2$-t-Bu | $CH_2Ph-4-Cl$ | $C(Me)_2CO_2H$ |
| 23 | H/H | benzothiazol-2-yl | $CH_2O$ | $CH_2$—Ph | $CH_2Ph-4-Cl$ | $C(Me)_2CO_2H$ |
| 24 | H/H | benzothiazol-2-yl | $CH_2O$ | $(CH_2)_2CH(Me)_2$ | $CH_2Ph-4-Cl$ | $C(Me)_2CO_2H$ |
| 25 | H/H | benzothiazol-2-yl | $CH_2O$ | $CH_2CH(Me)_2$ | $CH_2Ph-4-Cl$ | $C(Me)_2CO_2H$ |
| 26 | H/H | benzothiazol-2-yl | $CH_2O$ | $CH_2$-c-Pr | $CH_2Ph-4-Cl$ | $C(Me)_2CO_2H$ |
| 27 | 6-F/H | benzothiazol-2-yl | $CH_2O$ | $CH_2$-t-Bu | $CH_2Ph-4-Cl$ | $C(Me)_2CO_2H$ | which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Human Polymorphonuclear (PMN) Leukocyte $LTB_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13 M) or 5% (v/v) sodium heparin (1000 IU/mi). PMNs are isolated from anticoagulated blood by dextran sedimentation of erythrocytes followed by centrifugation through Ficoll-Hypaque (specific gravity 1.077), as described by Boyum (Scand. J. Clin. Lab. Invest., 21 (Supp. 97), 77(1968)). Contaminating erythrocytes are removed by lysis following exposure to ammonium chloride (0.16M) in Tris buffer (pH 7.65), and the PMNs resuspended at $5 \times 10^5$ cells/ml in HEPES (15 mill)-buffered Hanks balanced salt solution containing $Ca^{2+}$(1.4 mill) and $Mg^{2+}$(0.7 mill), pH 7.4. Viability is assessed by Trypan blue exclusion.

B. Generation and Radioimmunoassay of $LTB_4$ PMNs (0.5 mi; $2.5 \times 10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore A23187 (final concentration 10 mm) or vehicle in control samples and allowed to proceed for 5 minutes at 37° C. The reactions are then terminated by the addition of cold methanol (0.25 mi) and samples of the entire PMN reaction mixture removed for radioimmunoassay of $LTB_4$.

Samples (50 mi) of authentic $LTB_4$ of known concentration in radioimmunoassay buffer (RIA) buffer (potassium phosphate 1 MM; disodium EDTA 0.1 MM; Thimerosal 0.025 mm; gelatin 0.1%, pH 7.3) or PMN reaction mixture diluted 1:1 with RIA buffer are added to reaction tubes. Thereafter, $[^3H]$-$LTB_4$ (10 nCi in 100 mL RIA buffer) and $LTB_4$-antiserum (100 mL of a 1:3000 dilution in RIA buffer) are added and the tubes vortexed. Reactants are allowed to equilibrate by incubation overnight at 4° C. To separate antibody-bound from free $LTB_4$, aliquots (50 mi) of activated charcoal (3% activated charcoal in RIA buffer containing 0.25% Dextran T-70) are added, the tubes vortexed, and allowed to stand at room temperature for 10 minutes prior to centrifugation ($1500 \times g$; 10 min; 4° C). The supernatants containing antibody-bound $LTB_4$ are decanted into vials and Aquasol 2 (4 mi) added. Radioactivity is quantified by liquid scintillation spectrometry. The specificity of the antiserum and the sensitivity of the procedure have been described by Rokach et al. (*Prostaglandins Leukotrienes and Medicine*, 1984, 13, 21.) The amount of $LTB_4$ produced in test and control (approx. 20 ng/$10^6$ cells) samples is calculated. Inhibitory dose-response curves are constructed using a four-parameter algorithm and from these the $IC_{50}$ values are determined.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 ml/kg (intravenously) or 10 ml/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The invention is further defined by reference to the following examples, which are intended to be illustrative and not limiting. All temperatures are in degrees Celsius.

INTERMEDIATES

Preparation 1: Methyl 3-[1-(4-chlorobenzyl)-3-methyl-5-hydroxy-indol-2-yl]-2,2-dimethylpropanoate To a solution of 1.05 g (2.7 mmol) of 3-[1-(4-chlorobenzyl)-3-methyl-5-methoxyindol-2-yl]-2,2-dimethylpropanoic acid (EP 166,591, Example 22) and 800

μL of ethanethiol (10 mmol) in 20 mL of $CH_2Cl_2$ at −20° C. was added in portions 2.17 g (16 mmol) of $AlCl_3$. The reaction turned light orange and was stirred at room temperature overnight. In the morning, the reaction was completed (tlc) and it was poured into a solution of 1N HCl and extracted 3x with $CH_2Cl_2$. The combined organic layers were washed with brine, dried ($MgSO_4$), and filtered. The filtrate was evaporated and to the residual syrup (680 mg) was added 20 mL of $Et_2O$ followed by an ethereal solution of diazomethane. Evaporation of the solvent left the crude title compound which was used without further purification.

$^1$H NMR (250 MHz, $CDCl_3$): δ 7.3–7.15 (m, 3H, aromatic); 6.96 (m, 1H, aromatic): 6.70 (m, 3H, aromatic); 5.34 (s, 2H, N-CH2); 4.8–4.5 (M, 1H, —OH); 3.76 (s, 3H, —CO2Me); 3.12 (s, 2H, 2—CH2); 2.40 (S, 3H, 3-Me); 1.44 (s, 6H, C(Me)2).

Preparation 2: Methyl 3-[1-(4-chlorobenzyl)-3-(t-butylthio)-5-hydroxyindol-2-yl]-2,2-dimethylpropanoate The title compound was prepared as described in EP 419,049, Example 1, Step C.

Preparation 3: 3-[1-(4-Chlorobenzyl)-3-(t-butylthio)-5-hydroxyindol-2-yl]-2,2-dimethylpropanoic acid To a mixture of LiH (12.6 g) and HMPA (105 mi) in DMF (1050 mi) at 0° C. was added 2-methyl-2-propanethiol (178 mi). The mixture was stirred at room temperature for 30 min, then 3-[1-(4-chlorobenzyl)-3-(t-butylthio)-5-methoxyindol-2-yl]-2,2-dimethylpropanoic acid methyl ester (150 g) (EP 419,049, Example 1, Step A) in DMF (450 mi) was added slowly. The mixture was slowly heated to 150° C. and kept at that temperature for 18 hours. After cooling to room temperature, the supernatant layer was decanted and the residue dissolved in $H_2O$ and acidifed with 1N HCl, extracted twice with $Et_2O$, washed twice with brine, dried over $MgSO_4$, filtered and evaporated to dryness to provide the title compound.

Preparation 4: 3-[1-(4-Chlorobenzyl)-3-(t-butylthio)-5-hydroxyindol-2-yl]-2,2-dimethylpropanoic acid allyl ester The compound from Preparation 3 (150 g) was dissolved in DMF (1.2 L) then the solution was cooled in an ice-water bath. To this solution was added $K_2CO_3$ (138 g) portionwise and the mixture was left to stir for 30 min. Then allyl bromide (162 g) was added, the ice bath removed, and the mixture stirred for 18 hours. To the mixture was added aqueous $NH_4Cl$ and it was extracted with $Et_2O$. The organic layer was washed with $H_2O$ and brine, dried over $MgSO_4$, filtered, and evaporated to dryness. Purification by silica get chromatography afforded the title compound; m.p. 150°–151° C.

Preparation 5: 2-Bromomethylbenzothiazole

The title compound was prepared by photobromination (NBS, benzoylperoxide, hv) of 2-methylbenzothiazole (Aldrich) in $CCl_4$ followed by purification by silica gel chromatography. The compound can also be prepared as described in Chem. Abstr. 46, 6641b (1952).

EXAMPLE 5 m.p.=195°–197° C.

EXAMPLE 6 m.p.=210°–213° C.

EXAMPLE 7 m.p.=233°–236° C.

EXAMPLE 8

Analysis for $C_{33}H_{34}N_2O_4S_2ClNa \cdot H_2O$
Calc.: C, 59.75; H, 5.47; N, 4.22
Found: C, 59.56; H, 5.56; N. 4.24

EXAMPLE 9 m.p.=207°–209° C.

EXAMPLE 10 m.p.=245°–246° C.

EXAMPLE 11 m.p.=178.5°–181° C.

EXAMPLE 12

$^1$H NMR 300 MHz ($CD_3COCD_3$), δ 1.17 (9H, s), 1.22 (6H, s), 3.33 (2H, bs), 5.43 (2H, s), 5.55 (2H, s), 6.87–6.92 (3H, m), 7.25–7.28 (3H, m), 7.38–7.42 (3H, m), 7.65 (1H, dd), 7.72 ppm (1H, dd).

EXAMPLE 13

3-[1-(4-Chlorobenzyl)-3-methyl-5-(benzyothiazol-2-ylmethoxy)indol-2-yl]-2,2-dimethylpropanoic acid Step 1: Methyl 3-[1-(4-chlorobenzyl)-3-methyl-5-(benzothiazol-2-ylmethoxy)indol-2-yl]-2,2-dimethylpropanoate A solution of methyl 3-[1-(4-chlorobenzyl)-3-methyl-5-hydroxyindol-2-yl]-2,2-dimethylpropanoate (Preparation 1) (200 mg), 2-bromomethylbenzothiazole (147 mg), $Cs_2CO_3$ (263 mg) in 3 mL $CH_3CN$ and 3 mL DMF was stirred at 60° C. for 4 hours. The mixture was poured onto water, extracted with EtOAc, washed twice with brine, dried ($MgSO_4$), and evaporated. Chromatography of the residue on silica gel eluting with hexane/EtOAc 4:1 provided the title compound as a solid.

Step 2: 3-[1-(4-Chlorobenzyl)-3-methyl-5-(benzothiazol-2-ylmethoxy)indol-2-yl]-2,2-dimethylproyanoic acid The ester from Step 1 (265 mg) in 2.4 mL 1N LiOH, 3 mL THF, and 3 mL MEOH was heated to 50° C. for 4 hours. The solution was cooled, poured onto 1N HCl, extracted (3x EtOAc), washed twice with brine, dried ($MgSO_4$), and evaporated. Crystallization of the crude product from ether/hexane 2:1 provided the title compound as a solid; m.p. 181°–184° C.

EXAMPLE 14 m.p.=123°–126°-C.

EXAMPLE 15 m.p.=130°–131.5° C.

EXAMPLE 16 m.p.=187°–189° C.

EXAMPLE 17 m.p.=163°–165° C.

EXAMPLE 18 m.p.=186°-189° C.

EXAMPLE 19

3-[1-(4-Chlorobenzyl)-3-trimethylacetyl-5-(benzothiazol-2-ylmethoxy)indol-2-yl]-2,2-dimethylpropanoic acid Step 1: Methyl 3-[1-(4-chlorobenzyl)-3-trimethylacetyl-5-hydroxyindol-2-yl]-2,2-dimethylpropanoate To a solution of methyl 3-[1-(4-chlorobenzyl)-3-trimethylacetyl-5-(quinolin-2-ylmethoxy)indol-2-yl]-2,2-dimethylpropanoate (EP 419,049, March 27, 1991, Example 8, Step A) (11.5 g) in 150 mL DMF at 100° C. was added $CuCl_2 \cdot 2H_2O$ (4.9 g) in 26 mL $H_2O$. After 7 hours, the solution was cooled, poured onto aqueous $NH_4OAc$, and extracted with EtOAc. The organic phase was washed twice with $NH_4OAc$ (aq), washed with brine, dried ($MgSO_4$), and evaporated. Purification of the residue by chromatography on silica gel (8% EtOAc in toluene) gave the title compound as a brown gum.

Step 2:
3-[1-(4-Chlorobenzyl)-3-trimethylacetyl-5-hydroxyindol-2-yl]-2,2-dimethylpropanoic acid Following the procedure described in Example 13, Steps 1 and 2, but substituting the phenol from Step 1 for methyl 3-[1-(4-chlorobenzyl)-3-methyl-5-hydroxyindol-2-yl]-2,2-dimethylpropanoate as starting material, the title compound was obtained as a solid.

$^1$H NMR 300 MHz ($CD_3COCD_3$) δ 1.2 (6H, S), 1.3 (9H, s), 3.3 (2H, s), 5.54 (2H, s), 5.58 (2H, s), 6.4 (2H, d), 6.46 (1H, dd), 7.25-7.32 (4H, m), 7.45 (1H, t), 7.55 (1H, t), 8.0 (1H, d) and 8.03 ppm (1H, dd).

EXAMPLE 20

3-[1-(4-Chlorobenzyl)-3-(2,2-dimethylpropyl)-5-(benzothiazol-2-ylmethoxy)indol-2-yl]-2,2-dimethylpropanoic acid Step 1: Methyl 3-[1-(4-chlorobenzyl)-3-(2,2-dimethylpropyl)-5-(quinolin-2-ylmethoxy)indol-2-yl]-2,2-dimethylpropanoate A mixture of methyl 3-[1-(4-chlorobenzyl)-3-trimethylacetyl-5-(quinolin-2-ylmethoxy)indol-2-yl]-2,2-dimethylpropanoate (EP 419,049; Example 8, Step A) (15.64 g), $ZnI_2$ (25.2 g), and $NaBH_3CN$ (16.4 g) in 210 mL dichloroethane was stirred using a mechanical stirrer at r.t. for 30 minutes and then at 73° C. for 3 hours. The reaction mixture was allowed to cool, poured onto $NH_4OAc$ (aq), and extracted (3x EtOAc). The organic phase was dried ($MgSO_4$), evaporated, and the residue chromatographed (silica gel; ether/hexane 1:3) to give the title compound as a solid.

Step 2:
3-[1-(4-Chlorobenzyl)-3-(2,2-dimethylpropyl)-5-(quinolin-2-ylmethoxy)indol-2-yl]-2,2-dimethylpropanoic acid Following the procedure described in Example 19, Steps 1 and 2, but substituting the ester from Step 1 for methyl 3-[1-(4-chlorobenzyl)-3-trimethylacetyl-5-(quinolin-2-ylmethoxy)indol-2-yl]-2,2-dimethyl propanoate as starting material, the title compound was obtained as a solid; m.p. 172° C.

EXAMPLE 21 m.p.=175° C.

EXAMPLE 22 m.p.=192° C.

What is claimed is:
1. A compound of the formula I:

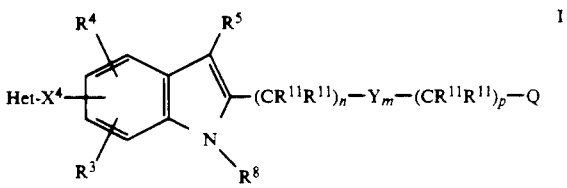

wherein:

Het is $ArR^1R^2$;

Ar is a bicyclic aromatic ring containing 8 or 9 members, one of which is O or S, and 0-2 of which is N, and the N-oxides thereof;

$R^1$, $R^2$, $R^3$, $R^4$ and $R^{10}$ are independently hydrogen, halogen, perhalo lower alkenyl, lower alkyl, lower alkenyl, lower alkynyl, —$CF_3$, —CN, —$NO_2$, —$N_3$, —$C(OH)R^{11}R^{11}$, —$CO_2R^{12}$, —$SR^{14}$, —S(O)$R^{14}$, —$S(O)_2R^{14}$, —$S(O)_2NR^{15}R^{15}$, —$OR^{15}$, —$NR^{15}R^{15}$, —$NR^{12}CONR^{15}R^{15}$, —$COR^{16}$, $CONR^{15}R^{15}$, or —$(CH_2)_rR^{21}$;

$R^5$ is hydrogen, —$CH_3$, $CF_3$, —C(O)H, $X^1$—$R^6$ or $X^2$—$R^7$;

$R^6$ and $R^9$ are independently alkyl, alkenyl, —($CH_2$)$_u$Ph($R^{10}$)$_2$ or —($CH_2$)$_u$Th($R^{10}$)$_2$ wherein Ph is phenyl and Th is 2- or 3-thienyl;

$R^7$ is —$CF_3$ or $R^6$;

$R^8$ is hydrogen or $X^3$-$R^9$ each $R^{11}$ is independently hydrogen or lower alkyl, or two $R^{11}$'s on same carbon atom are joined to form a cycloalkyl ring of 3 to 6 carbon atoms;

$R^{12}$ is hydrogen, lower alkyl or —$CH_2R^{21}$;

$R^{13}$ is lower alkyl or —$(CH_2)_rR^{21}$;

$R^{14}$ is —$CF_3$ or $R^{13}$;

$R^{15}$ is hydrogen, —$COR^{16}$, $R^{13}$, of two $R^{15}$'s on the same nitrogen may be joined to form a monocyclic heterocyclic ring of 4 to 6 atoms containing up to 2 heteroatoms chosen from O, S, or N;

$R^{16}$ is hydrogen, —$CF_3$, lower alkyl, lower alkenyl, lower alkynyl or —$(CH_2)_rR^{21}$;

$R^{17}$ is —$(CH_2)_s$—$C(R^{18}R^{18})$—$(CH_2)_s$—$R^{19}$ or —$CH_2CONR^{15}R^{15}$.

$R^{18}$ is hydrogen or lower alkyl;

$R^{19}$ is a) a monocyclic or bicyclic heterocyclic ring containing from 3 to 9 nuclear carbon atoms and 1 or 2 nuclear hetero-atoms selected from N, S or O and with each ring in the heterocyclic radical being formed of 5 or 6 atoms, or
b) the radical W—$R^{20}$;

$R^{20}$ is alkyl or —$COR^{23}$;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, —$CF_3$, —CN, —$NO_2$ or —$N_3$;

$R^{23}$ is alkyl, cycloalkyl, or monocyclic monoheterocyclic ring;

$R^{24}$ is the residual structure of a standard amino acid, or $R^{18}$ and $R^{24}$ attached to the same N can cyclize to form a proline residue;

m is 0 or 1;

n is 0 to 3;
p is 1 to 3 when m is 1;
p is 0 to 3 when m is 0;
r is 0 to 2;
s is 0 to 3;
t is 0 to 2;
u is 0 to 3;
W is O, S or $NR^{15}$;
$X^1$ is O or $NR^{15}$;
$X^2$ is CO, $CR^{11}R^{11}$, S, S(O), or $S(O)_2$;
$X^3$ is CO, $CR^{11}R^{11}$, $S(O)_2$, or a bond;
$X^4$ is CH=CH, $CH_2$—yl, or $Y^1$—$CH_2$;
Y is $X^1$ or $X^2$;
$Y^1$ is O, S, $S(O)_2$, or $CH_2$;
Q is —$CO_2R^{12}$, —$CONHS(O)_2R^{14}$, —$NHS(O)_2R^{14}$, —$S(O)_2NHR^{15}$, —$CONR^{15}R^{15}$, —$CO_2R^{17}$, —$CONR^{18}R^{24}$, —$CR^{11}R^{11}OH$, or 1H- or 2H-tetrazol-5-yl;
or a pharmaceutically acceptable salt thereof.

2. A compound of claim 1 wherein $X^4$ is $CH_2$-$Y^1$ and $Y^1$ is O;
or a pharmaceutically acceptable salt thereof.

3. A compound of claim 1 wherein:
$R^1$, $R^2$, $R^3$, and $R^4$ are hydrogen;
$R^5$ is $X^2$—$R^7$;
$R^7$ is $R^6$;
$R^8$ is $R^9$;
$R^{10}$ is hydrogen or halogen;
m is 0;
n is 1 to 3;
u is 0 in $R^6$ and 1 in $R^9$;
$X^2$ is $CR^{11}R^{11}$ or S;
$X^4$ is $CH_2$—$Y^1$;
$Y^1$ is 0; and
Q is —$CO_2R^{12}$;
or a pharmaceutically acceptable salt thereof.

4. The compound of claim 1 wherein:
$R^1$, $R^2$, $R^3$, and $R^4$ are hydrogen;
$R^5$ is $X^2$—$R^7$;
$R^7$ is $R^6$;
$R^8$ is $R^9$;
$R^{10}$ is hydrogen or halogen;
m is 0;
n is 1 to 3;
u is 0 in R6 and 1 in $R^9$;
$X^2$ is $CR^{11}R^{11}$ or S;
$X^4$ is $CH_2$—$Y^1$;
$Y^1$ is 0; and
Q is 1-H- or 2H-tetrazol-5-yl;
or a pharmaceutically acceptable salt thereof.

5. A compound of claim 1 of the formula Ia:

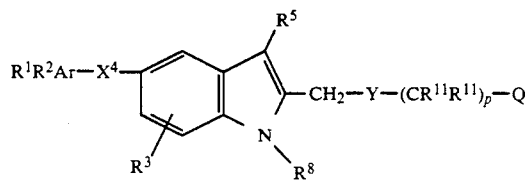

wherein the substituents are as follows:

| Ex No. | $R^1/R^2$ | Ar | $X^4$ | $R^5$ | $R^8$ | Y—$(CR^{11}R^{11})_p$—Q |
|---|---|---|---|---|---|---|
| 1 | H/H | benzo[b]furan-2-yl | $CH_2O$ | Me | $CH_2Ph$-4-Cl | $C(Me)_2CO_2H$ |
| 2 | 5-Cl/H | benzothiazol-2-yl | $CH_2O$ | S-t-Bu | $CH_2Ph$-4-Cl | $C(Me)_2CO_2H$ |
| 3 | H/H | thieno[2,3-b]pyridin-6-yl | $CH_2S$ | $COCH_2$-t-Bu | $CH_2Ph$-3-CN | $C(Me)_2CONHS(O)_2Me$ |
| 4 | H/H | furo[3.2-b]pyridin-5-yl | $CH_2CH_2$ | S—Ph | $CH_2PhS(O)_2Me$ | $C(Me)_2CHOHMe$ |
| 5 | H/H | benzothiazol-2-yl | $CH_2O$ | S-t-Bu | $CH_2Ph$-4-Cl | $C(Me)_2CO_2H$ |
| 6 | 5-F/H | benzothiazol-2-yl | $CH_2O$ | S-t-Bu | $CH_2Ph$-4-Cl | $C(Me)_2CO_2H$ |
| 7 | 5-$CF_3$/H | benzothiazol-2-yl | $CH_2O$ | S-t-Bu | $CH_2Ph$-4-Cl | $C(Me)_2CO_2H$ |
| 8 | 6-OMe/H | benzothiazol-2-yl | $CH_2O$ | S-t-Bu | $CH_2Ph$-4-Cl | $C(Me)_2CO_2H$ |
| 9 | 2-Me/H | benzothiazol-5-yl | $CH_2O$ | S-t-Bu | $CH_2Ph$-4-Cl | $C(Me)_2CO_2H$ |
| 10 | 5,6-$F_2$ | benzothiazol-2-yl | $CH_2O$ | S-t-Bu | $CH_2Ph$-4-Cl | $C(Me)_2CO_2H$ |
| 11 | H/H | benzothiazol-2-yl | $CH_2O$ | $COCH_2$-t-Bu | $CH_2Ph$-4-Cl | $C(Me)_2CO_2H$ |
| 12 | H/H | benzoxazol-2-yl | $CH_2O$ | S-t-Bu | $CH_2Ph$-4-Cl | $C(Me)_2CO_2H$ |
| 13 | H/H | benzothiazol-2-yl | $CH_2O$ | Me | $CH_2Ph$-4-Cl | $C(Me)_2CO_2H$ |
| 14 | H/H | benzothiazol-2-yl | $CH_2O$ | t-Bu | $CH_2Ph$-4-Cl | $C(Me)_2CO_2H$ |
| 15 | H/H | benzothiazol-2-yl | $CH_2O$ | H | $CH_2Ph$-4-Cl | $C(Me)_2CO_2H$ |
| 16 | H/H | benzothiazol-2-yl | $CH_2O$ | CO-c-Bu | $CH_2Ph$-4-Cl | $C(Me)_2CO_2H$ |
| 17 | H/H | benzothiazol-2-yl | $CH_2O$ | $CH_2$-c-Bu | $CH_2Ph$-4-Cl | $C(Me)_2CO_2H$ |
| 18 | 5-F/H | benzothiazol-2-yl | $CH_2O$ | $COCH_2$-t-Bu | $CH_2Ph$-4-Cl | $C(Me)_2CO_2H$ |
| 19 | H/H | benzothiazol-2-yl | $CH_2O$ | CO-t-Bu | $CH_2Ph$-4-Cl | $C(Me)_2CO_2H$ |
| 20 | H/H | benzothiazol-2-yl | $CH_2O$ | $CH_2$-t-Bu | $CH_2Ph$-4-Cl | $C(Me)_2CO_2H$ |
| 21 | 5-F/H | benzothiazol-2-yl | $CH_2O$ | CO-t-Bu | $CH_2Ph$-4-Cl | $C(Me)_2CO_2H$ |
| 22 | 5-F/H | benzothiazol-2-yl | $CH_2O$ | $CH_2$-t-Bu | $CH_2Ph$-4-Cl | $C(Me)_2CO_2H$ |
| 23 | H/H | benzothiazol-2-yl | $CH_2O$ | $CH_2$—Ph | $CH_2Ph$-4-Cl | $C(Me)_2CO_2H$ |
| 24 | H/H | benzothiazol-2-yl | $CH_2O$ | $(CH_2)_2CH(Me)_2$ | $CH_2Ph$-4-Cl | $C(Me)_2CO_2H$ |
| 25 | H/H | benzothiazol-2-yl | $CH_2O$ | $CH_2CH(Me)_2$ | $CH_2Ph$-4-Cl | $C(Me)_2CO_2H$ |
| 26 | H/H | benzothiazol-2-yl | $CH_2O$ | $CH_2$-c-Pr | $CH_2Ph$-4-Cl | $C(Me)_2CO_2H$ |
| 27 | 6-F/H | benzothiazol-2-yl | $CH_2O$ | $CH_2$-t-Bu | $CH_2Ph$-4-Cl | $C(Me)_2CO_2H$. |

6. A pharmaceutical composition comprising a therapeutically effective amount of a compound of claim 1 and a pharmaceutically acceptable carrier.

7. A method of preventing the synthesis, the action, or the release of SRS-A or leukotrienes in a mammal which comprises administering to said mammal an effective amount of a compound of claim 1.

* * * * *